United States Patent
Pinapala Venkata et al.

(10) Patent No.: US 9,112,960 B2
(45) Date of Patent: Aug. 18, 2015

(54) BLOOD ALCOHOL CONTENT MEASUREMENT SYSTEM POWERED BY AN AUDIO SIGNAL FROM A PHONE

(71) Applicant: Cyberliver Limited, Stanmore (GB)

(72) Inventors: Bharadwaj Ragavendra Prasad Pinapala Venkata, Chennai (IN); Ravi Kumar Kalkivayi Seshagiri, Westhoughton (GB)

(*) Notice: Subject to any disclaimer, the term of this patent is extended or adjusted under 35 U.S.C. 154(b) by 36 days.

(21) Appl. No.: 14/082,405

(22) Filed: Nov. 18, 2013

(65) Prior Publication Data

US 2014/0141837 A1 May 22, 2014

(30) Foreign Application Priority Data

Nov. 19, 2012 (GB) .................. 1220772.6

(51) Int. Cl.
*H04M 1/21* (2006.01)
*H04M 1/725* (2006.01)
*G01N 33/497* (2006.01)

(52) U.S. Cl.
CPC ............ *H04M 1/21* (2013.01); *H04M 1/72522* (2013.01); *G01N 33/4972* (2013.01); *H04M 2250/52* (2013.01)

(58) Field of Classification Search
None
See application file for complete search history.

(56) References Cited

U.S. PATENT DOCUMENTS

2010/0003647 A1* 1/2010 Brown et al. .................. 434/127
2014/0062722 A1* 3/2014 Ofir et al. .................. 340/870.02
2014/0300722 A1* 10/2014 Garcia ............................ 348/77

* cited by examiner

*Primary Examiner* — Charles Appiah
*Assistant Examiner* — Margaret G Mastrodonato
(74) *Attorney, Agent, or Firm* — The Law Office of Austin Bonderer, PC

(57) ABSTRACT

A blood alcohol content (BAC) measurement system powered by an audio signal from a phone is provided. The BAC measurement system includes a sensor unit, a microcontroller and a power extraction unit. The sensor unit includes a fuel cell that generates an electric current when a breath of a user contacts the fuel cell. The microcontroller generates a signal based on the electric current. A frequency of the signal is based on alcohol content in the breath. The power extraction unit powers the sensor unit. The power extraction unit converts the audio signal generated by the phone into power for the microcontroller.

7 Claims, 7 Drawing Sheets

BLOOD ALCOHOL CONTENT MEASUREMENT SYSTEM POWERED BY AN AUDIO SIGNAL FROM A PHONE

BACKGROUND

1. Technical Field

The embodiments herein generally relate to alcohol management systems, and, more particularly, to an alcohol management system, powered by an audio signal, for measuring a blood alcohol content of a user.

2. Description of the Related Art

There exist a number of portable breathalyzers, as well as alcohol consumption trackers which enable an individual to keep track of their drinking habits. However, to date these have generally not been combined in a system which may be readily used by an individual and which may give guidance to the individual on a real time basis.

There are various forms of breathalyzers, including breathalyzers based on chemical reactions which indicates blood alcohol concentration by a change in colour, battery powered electronic breathalyzers and re-usable smartphone powered breathalyzers.

The "iBreath Alcohol Breathalyzer" is a device which can be plugged into the base of an iPhone™ or an iPod™. The breathalyzer estimates the blood alcohol concentration (BAC) of an individual, by detecting and measuring the presence of ethanol vapour in the individual's breath. The breathalyzer comprises a semiconductor sensor chip, including a thin membrane of tin dioxide. Connected to the membrane is a small metal heater, which takes power from the iPhone™ or iPad™, to warm up the membrane to an optimal operating temperature. When ethanol gas comes into contact with the tin dioxide membrane, the membrane absorbs the ethanol molecules and the electrical resistance of the membrane changes. A measurement of the changes in resistance gives an estimate of the individual's BAC which can be shown to be related to the presence of ethanol vapour in the breath. Whilst such a device gives the individual a useful indication of whether their BAC exceeds a set amount, for example so as to enable the decision not to drive, this device does not give the user other information which he might use to change his behavior to avoid further instances of high blood alcohol content There also exist a number of smartphone applications, including means for monitoring the number of drinks consumed.

AlcoDroid Alcohol Tracker, developed by Myrecek discloses an alcohol consumption tracker application for a mobile phone, in which the individual logs the drinks which have been consumed. The EAC is plotted on a chart which is displayed by the mobile phone. This indicates when the individual reaches the legal limit for drinking and driving, or subsequently when the BAC gets back to zero.

Blood Alcohol Calculator developed by Hauki, is an application for a mobile phone, in which the individual may type in the number of drinks of various types, that is beer, wine, spirits and the maximum blood alcohol is calculated and displayed.

Alcohol Calculator developed by Pawel Nadolski, is also an alcohol calculator application for a mobile phone. The individual must enter the number of alcoholic drinks and the time at which they were consumed, to enable the application to display the concentration of alcohol in the blood and the estimated time when the level will drop to an allowable drink driving time.

The Blood Alcohol Calculator developed by CityJams includes a simple calculator, including a list of common drink types. The individual must enter their weight, the hours that have been spent drinking and the types of drinks. The Blood Alcohol Calculator then calculates the BAC.

The Drink Droid Plus BAC Calculator developed by Laby, is an application for a blood alcohol content calculator which estimates the BAC based on the number and types of drinks which have been entered by the individual. A link may be included to the telephone number of a transportation service provider to enable the transportation service provider, to be contacted, when the individual is over the drink and drive limit. You See Pro, developed by NeatWits, is an application for a smartphone in which the individual can record a diary of drinks consumed, to keep track of alcohol consumption.

A further example of a blood alcohol content calculator is jAlcoMeter, developed by Tuukka Haapasalo. The application works by allowing a user to enter each drink as he/she drinks, or later if he/she forgets to add the information at the time. Personal information such as gender and weight is entered to enable the BAC estimation calculation to work correctly. The current intoxication level is indicated. However, whilst this application gives an indication of how intoxicated a person is becoming, it is necessary for the individual to enter details of each drink consumed, which is likely in the circumstances to be inaccurate. There is no possibility of any feedback which would enable them to modify their habits or obtain any indication of whether their drinking habits have caused any long term problem.

KR 100286129 discloses a portable phone having a "drunkometer" function to add the functions of a breathalyzer to a portable terminal A "drunken alarm message" display on the portable phone is connected to an alcohol concentration detection sensor. A ROM connected with the message display, stores the required drunken alarm messages.

Thus whilst portable breathalyzers exist and mobile device applications operable to enable an individual to log the number of drinks consumed exist, there is no alcohol management system available, which gives the individual an easily usable means of correlating breathalyzer information to any potential problems relating to his/her lifestyle and alcohol consumption.

SUMMARY

In view of the foregoing, an embodiment herein provides a blood alcohol content (BAC) measurement system powered by a continuous audio signal from a phone. The BAC measurement system includes a sensor unit, a microcontroller and a power extraction unit. The sensor unit includes a fuel cell that generates an electric current when a breath of a user contacts the fuel cell. The microcontroller generates a signal based on the electric current, wherein a frequency of the signal is based on an alcohol content in the breath. The power extraction unit that powers the sensor unit converts the continuous audio signal generated by the phone into power for the microcontroller. A frequency of the continuous audio signal may range from 15000 Hz to 18000 Hz.

The blood alcohol content (BAC) measurement may further include (a) a camera that captures an image of an alcoholic drink, and (b) a pattern recognition unit responsive to an image captured by the camera, that obtains information relating to the image.

The pattern recognition unit includes edge recognition unit to interpret a shape of a beverage container. The pattern recognition unit includes a bar code reader responsive to a bar code in the image.

In another aspect, a blood alcohol content (BAC) measurement system that measures a blood alcohol content of a user is provided. The BAC measurement system includes a phone and a breathalyzer unit. The phone that generates a continuous audio signal includes a camera, a pattern recognition and a display unit. The camera captures an image of an alcoholic drink. The pattern recognition unit responsive to an image captured by the camera and obtains information relating to the image. The display unit displays a BAC of the user. The breathalyzer unit includes a sensor unit, a microcontroller and a power extraction unit. The sensor unit includes a fuel cell that generates an electric current when a breath of a user contacts the fuel cell. The microcontroller generates a signal based on the electric current. A frequency of the signal is based on an alcohol content in the breath. The power extraction unit that powers the sensor unit converts the continuous audio signal generated by the phone into power for the microcontroller. A frequency of the continuous audio signal may range from 15000 Hz to 18000 Hz. The breathalyzer unit is connected to the phone through an audio jack of the phone.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1:
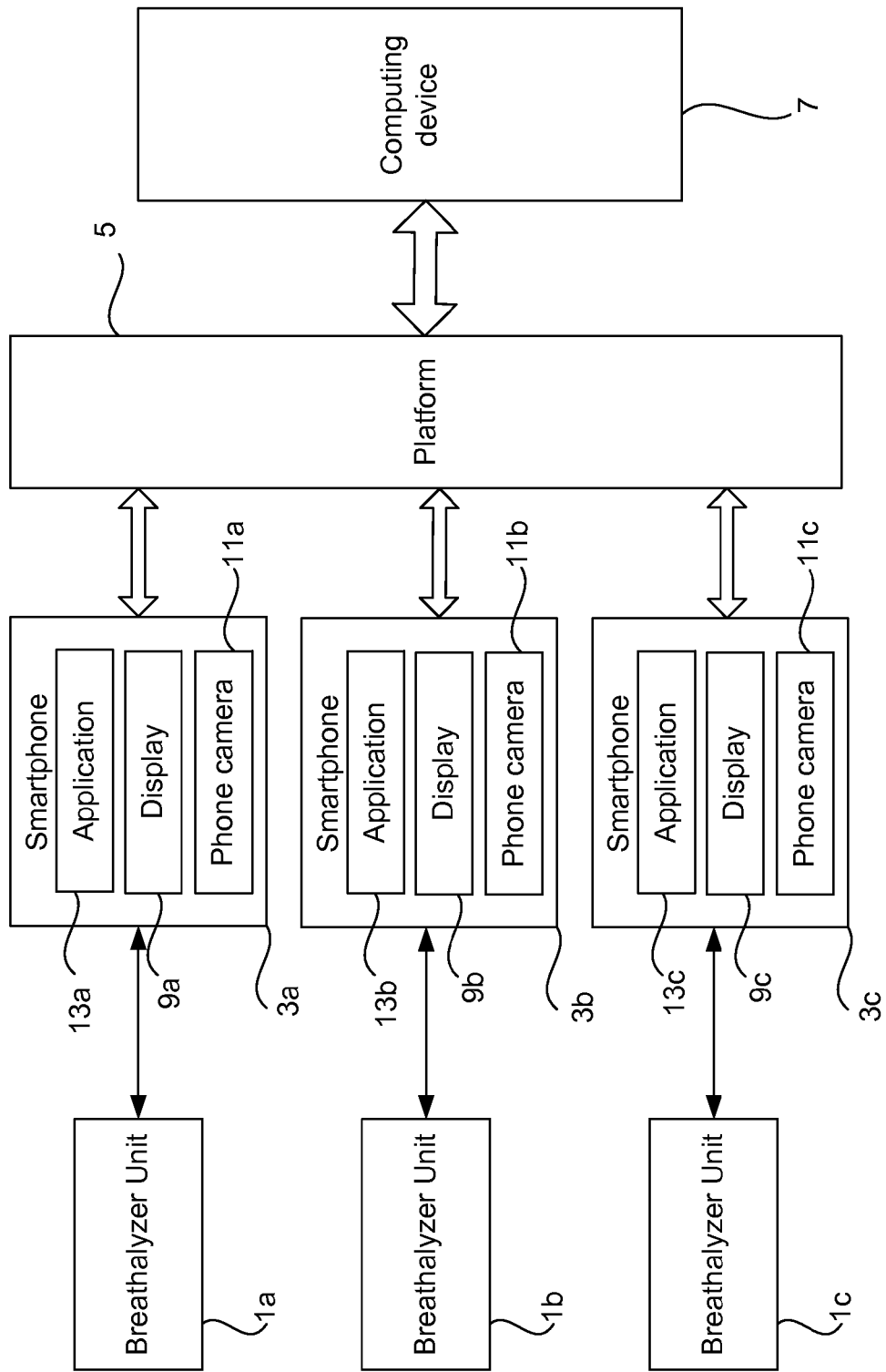
FIG. 1 illustrates an overall view of the alcohol management system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system that gives an individual an easily usable means of correlating breathalyzer information to any potential problems relating to his/her lifestyle and alcohol consumption. The embodiments herein achieve this by providing an alcohol management system that includes a breathalyzer of a portable nature, which can be used by an individual to monitor their alcohol consumption. The alcohol management system has particular application in giving the individual a possibility of being able to adjust their drinking behavior if necessary, based on information provided by the breathalyzer. Referring now to the drawings, and more particularly to FIGS. 1 through 7, where similar reference characters denote corresponding features consistently throughout the figures, there are shown preferred embodiments.

FIG. 1 illustrates an overview of an alcohol management system in accordance with an embodiment herein. A user of the system is provided with a breathalyzer unit 1a, 1b, 1c, which the user may connect with the smartphones 3a, 3b, and 3c. It will be appreciated that in the figure, only three users are shown: in practice of course there will be a great deal more users. Each phone 3a, 3b, and 3c is arranged to be in telephone communication with a platform 5, under the control of a computing device 7.

Each phone 3a, 3b, 3c will include the usual smartphone functions (e.g., a mobile communication device that has smart features), such as a keyboard to enable the user to interact with the phone and the usual telecommunication functions. However, to provide clarity, only the display 9a, 9b, 9c on each phone is illustrated, together with the phone camera 11a, 11b, 11c. Each of the smartphone includes a client application (e.g., an alcohol management system application) that is executed to manage BAC of the user. In other words, the alcohol management system application 13a, 13b, and 13c are installed and/or executed, on each smartphone 3a, 3b, 3c, as will be described in more detail hereafter.

In use of the system, each user is able to obtain blood alcohol content (BAC) reading using the respective breathalyzer unit 1a, 1b, 1c which is powered by the respective smartphone 3a, 3b, and 3c. Information relating to the readings is transferred via the telephone communication system between the smartphone 3a, 3b, 3c and the platform 5, under the control of the computing device 7. The platform 5 provides each user with personal information based on an analysis of their BAC data and other data which is received from the users via their respective smartphone 3a, 3b, and 3c.

Figure 2:
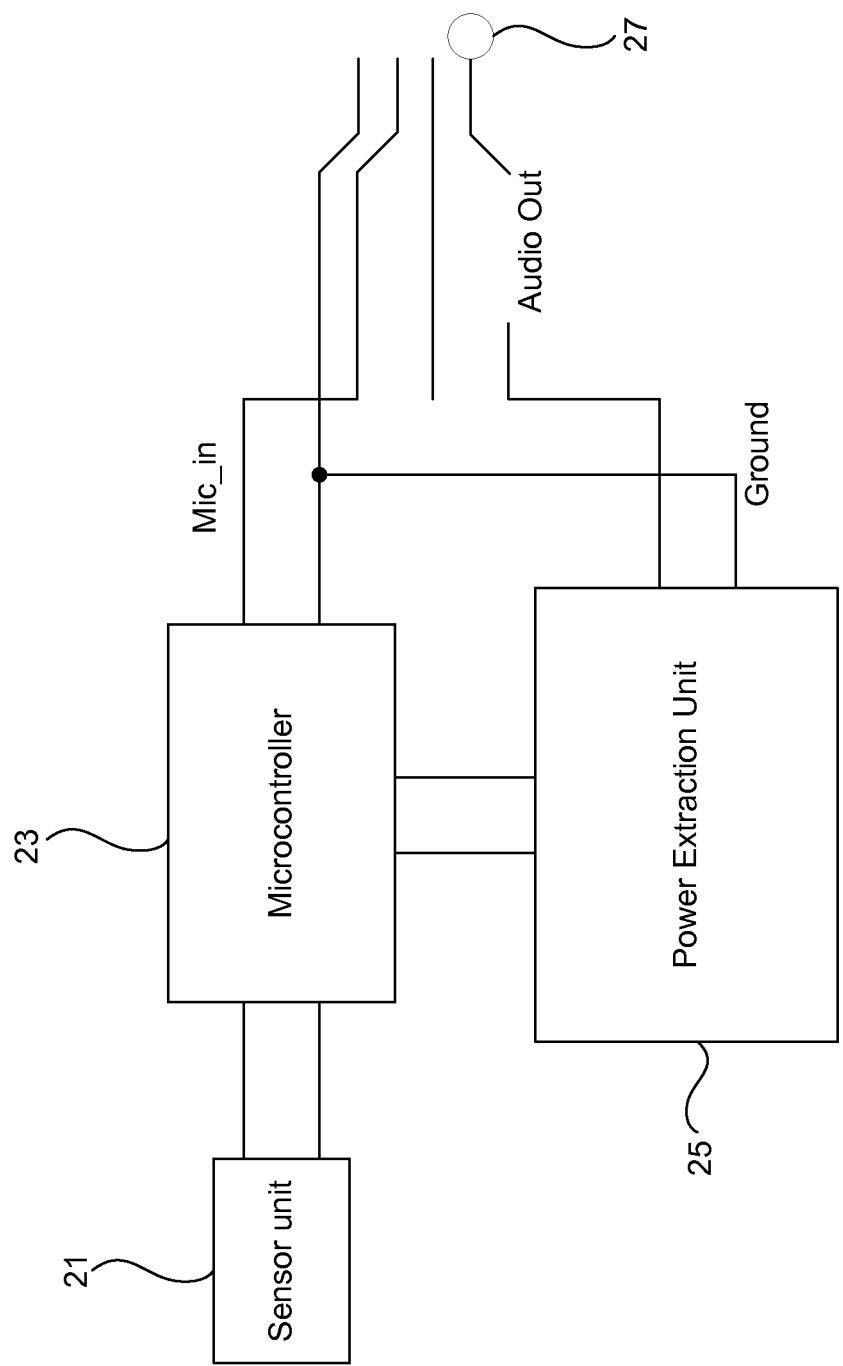
FIG. 2 illustrates a schematic diagram of the circuit of the breathalyzer unit incorporated in the system of FIG. 1 according to an embodiment herein.

With reference to FIG. 1, FIG. 2 illustrates schematically the circuitry which is used to power each breathalyzer unit 1a, 1b, 1c according an embodiment herein. More particularly, FIG. 2 illustrates a schematic diagram of the circuit of the breathalyzer unit incorporated in the system of FIG. 1 according to an embodiment herein. Each breathalyzer unit 1a, 1b, 1c includes a fuel cell sensor unit 21, a microcontroller 23, and a power extraction unit 25. The power extraction unit 25 and microcontroller 23 are connected to a plug 27, designed to be inserted in the jack (not shown) of a smartphone. The power extraction unit 25 is designed to extract power from the user's smartphone, so as to avoid the necessity of providing a battery for the breathalyzer. The alcohol management system application 13 (e.g. a smartphone application not shown in FIG. 2) loaded in the smartphone 3 (not shown in FIG. 2), is arranged to cause the smartphone 3 to send out an audio signal to the power extraction unit 25, which in turn converts the signal into the required power for the microcontroller 23, which in turn powers the sensor unit. The microcontroller 23 generates a signal based on the electric current. A frequency of the signal is based on alcohol content in the breath, in one example embodiment. The audio signal is a continuous audio signal that is transmitted to the power extraction unit, in one example embodiment. The audio signal may be transmitted at one or more intervals (e.g., the audio signal may not be a continuous audio signal), in which case the power extraction unit may accordingly convert the audio signal into power, in another example embodiment. Once the microcontroller 23 receives the power, the microcontroller 23 initializes and sends a 1 KHz continuous audio signal to the smartphone 3 to indicate that the breathalyzer unit 1 is ready to blow. When the breathalyzer unit 1 sends the 1 KHZ continuous audio signal to the smartphone 3, the alcohol management system application 13 allows the user to exhale air into the breathalyzer unit 1. In one embodiment, a frequency of the continuous audio signal ranges from 15000 Hz to 18000 Hz.

When the user breathes onto the powered sensor unit 21, the breath of the user contacts the fuel cell in the sensor unit 21. The sensor unit 21 generates an electric current, which is measured by the microcontroller 23, amplified and generates a signal whose frequency depends on the amount of alcohol in the user's breath. The electric current sensed by sensor unit 21 produces a voltage, and the obtained voltage is converted to an audio signal whose frequency is determined by using a formula: FREQUENCY={(Volt*1023/1.8)+100}*10 Hz. A signal representative of the frequency, passes through the mic-in line to the smartphone 3. The smartphone application 13 identifies the frequency of the signal and displays a BAC value on the display 9 of the smartphone 3. The smartphone application 13 uses the Fast Fourier transform (FFT) principle to identify the frequency of the signal that the smartphone 3 receives from the breathalyzer unit 1, and converts the identified frequency of the signal to respective BAC (Blood Alcohol Content) in percentage using the formula: BAC=((Frequency−1000 Hz)/75*100), where 1000 is the default synchronization frequency in Hz, and 75 is to convert frequency to respective BAC (e.g., 75 Hz=1 unit of BAC). It is to be understood to a person having ordinary skill in the art that other principles may be implemented into the smartphone 13 to identify the frequency of the signal that the smartphone 3 receives from the breathalyzer unit 1, and converts the identified frequency of the signal to respective BAC (Blood Alcohol Content).

It will be appreciated that as the breathalyzer unit 1 is highly portable and is disposable in nature, it is of such a form that the user can easily carry it in a pocket, use it and dispose of it after usage.

Figure 3:
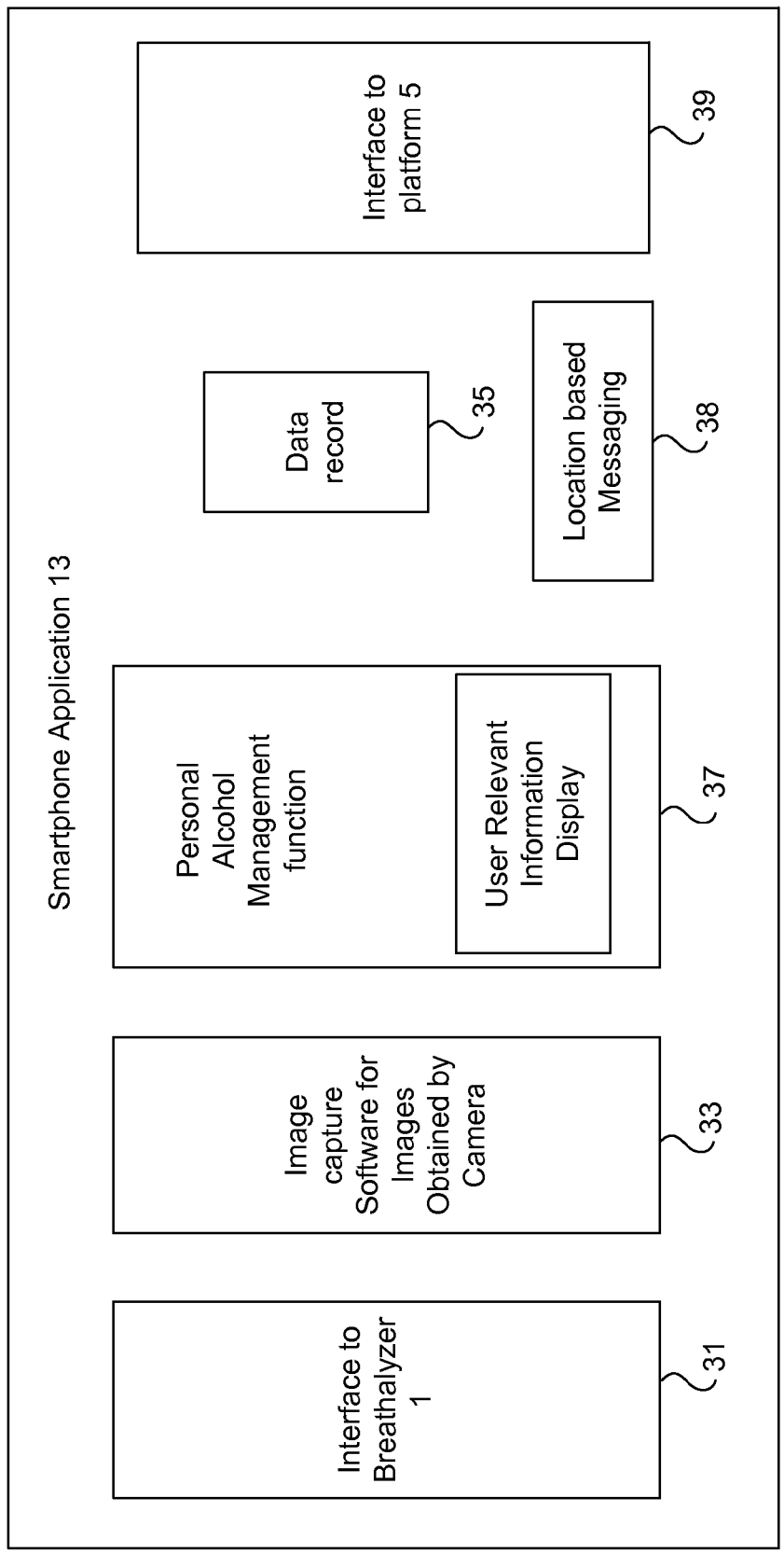
FIG. 3 illustrates details of the application loaded on each user's smartphone according to an embodiment herein.
Figure 4:
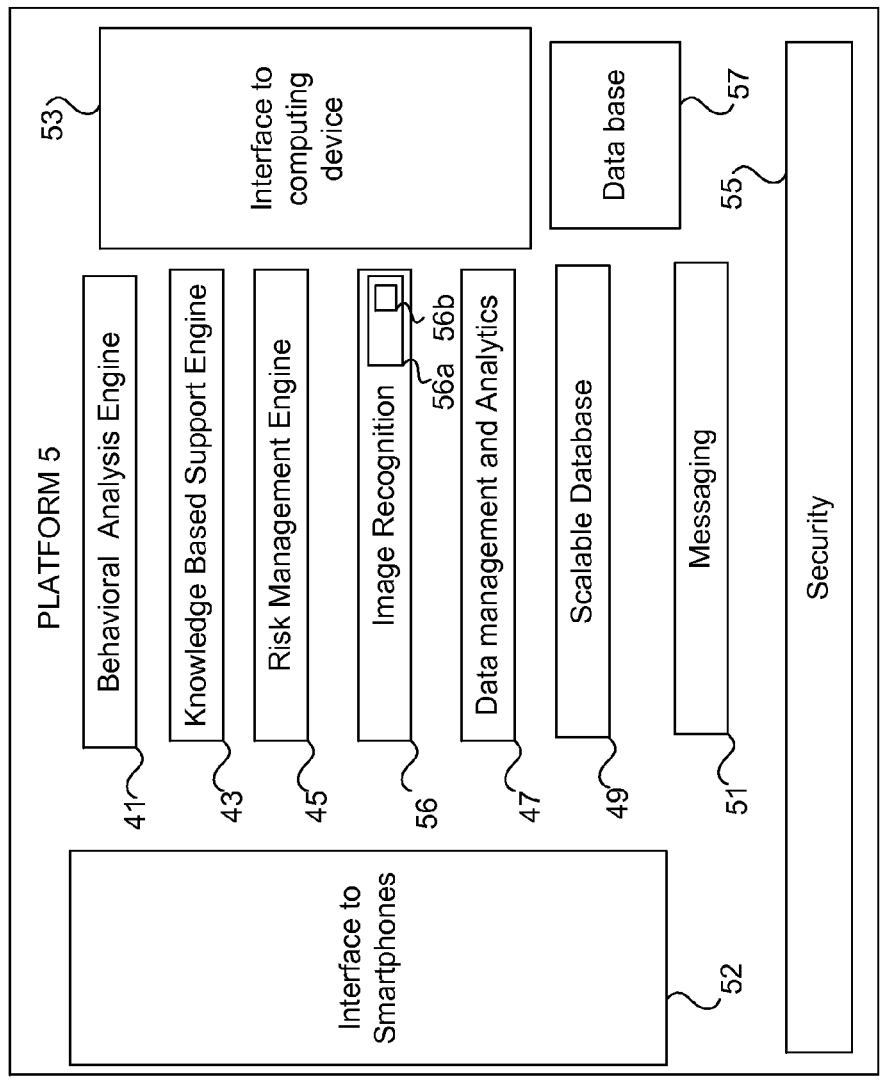
FIG. 4 is a schematic illustration of the main features of the platform according to an embodiment herein.
Figure 5:
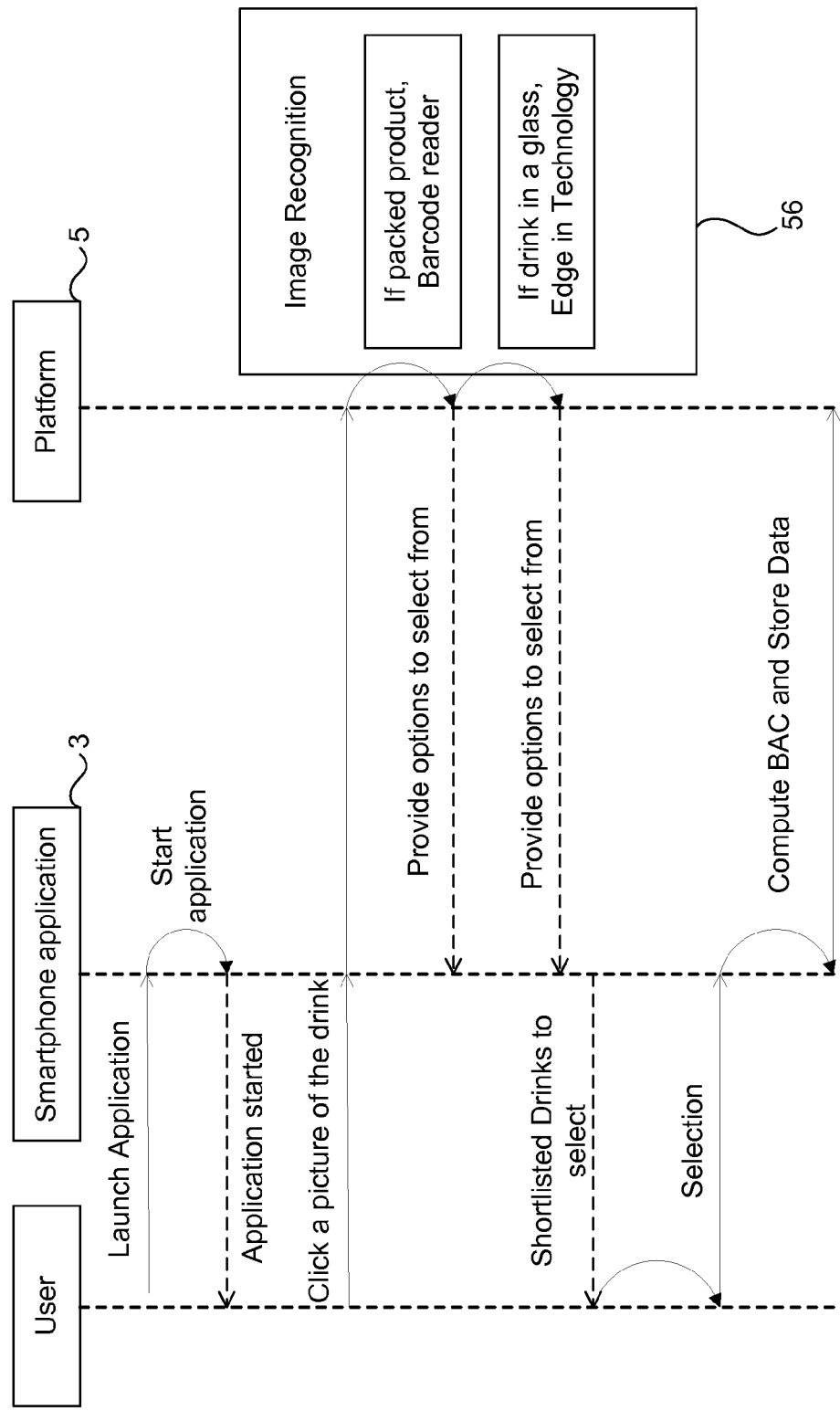
FIG. 5 illustrates the operation of the image recognition algorithm on the smartphone according an embodiment herein.

With reference to FIGS. 1-2, FIG. 3 illustrates details of the application 13 loaded on each user's smartphone 3 according to an embodiment herein. Whilst the system is being described in relation to the application is designed to run on any suitable mobile device, including an iOS Android, Blackberry or Windows smartphone. The application enables the user to record alcohol consumption every time the breathalyzer is used via the interface 31 to the breathalyzer 1a, 1b, 1c.

The application 13 also includes an image capture software 33 for images of drinks which a user may capture using the phone camera 11 on their phone 3, which interacts with an image recognition function on the platform 5 to provide a drink recognition function as will be described in more detail hereafter.

A personal alcohol manager function 37 within the application 13, will assist users to monitor their alcohol consumption in a number of ways. In particular the personal alcohol management function 37 may recognize inputs from social websites (e.g., Facebook®), relating to locations where alcohol may be consumed and other social media and causes a message on the display 9 to remind users to specify any alcohol consumed during the time spent in the recognized location. This information is stored in the data record 35, text messaging in the display 9 being used to nudge (e.g., alert or notify) the user to remind them to self-monitor their alcohol consumption.

The breathalyzer unit PAM results and the drink recognition results are also linked to a diary system, located within the data record 35 which provides an appropriate diary display on the phone display. The diary acts via the personal alcohol management function 37, to help users maintain a visual record on the phone display of the units of alcohol consumed. Inbuilt mechanisms are provided to warn (or alert or notify) users when they have reached a daily, weekly or monthly limit. Other information is provided to provide the user with measurement tools such as CAGE and AUDIT-C questionnaires to identify users that may have alcohol dependent syndrome. CAGE and AUDIT-C are tests which help an individual assess effects of alcohol consumption on them. Details of these tests are found in for example http://en.wikipedia.org/wiki/CAGE_questionnaire and http://en.wikipedia.org/wiki/Alcohol_Use_disorders_Identification_Test#cite_note-1. Links may be provided to interface directly to RSS feeds and websites which provide direct advice on alcohol dependence.

The management function 37 is also linked to a location based message system 38, which can be integrated with taxi companies with an SMS gateway. When an alert function is generated by the personal alcohol function 37 the user will be prompted to contact an emergency contact or order a transport facility (e.g., a taxi service provider for booking a taxi from a source to destination). If they choose to order a taxi, a text message can be arranged to be sent from the phone to the nearest partner taxi company. Alternatively or additionally the location of the user using the GPS or GPRS function on the smartphone, can be sent to an emergency contact via an SMS transmitted from the phone so as to help the user accordingly. The smartphone application 13 will interact via interface 39 with the platform 5. The smartphone 3a, 3b, and 3c and the smartphone application 13 may further include an input unit that receives input from a user on drink options generated based on the information relating to the image With reference to FIGS. 1 through 3, FIG. 4 is a schematic illustration of the main features of the platform 5 according to an embodiment herein. The platform 5 has a number of engines 41, 43, 45, 47 and a scalable database 49. The behavioral analysis engine 41 analyses data collected from various users via the interface 51 and is able to engage with the users, by sending them appropriate messages. The knowledge base support engine 43 also provides facts, news and updates via RSS feeds to the users in able to encourage them keep their awareness of alcohol consumption. The risk management engine 45 analysis the data received from the smartphones and computes if the users are at risk. If any potential risks are found, the users are sent relevant warning messages to their phones 3 via the messaging unit 51. The data management and analytical engine 47 manages the incoming data and provides an analysis of trends in the data. The messaging engine 51 has adaptors built for various communication modes such as SMS, e-mail and web services and helps the platform to communicate with the users, via the interface 52. An interface 53 interacts with the computing device 7. Appropriate security measures 53 are built into the platform 5, to avoid infiltration from unauthorized parties, for example via the use of passwords on the phones 3. A security 55 for handling security measures in the platform 5. An image recognition unit 56 to identify the images (e.g., of alcoholic drinks) captured by the user from a camera of the smartphone 3a or 3b or 3c. The image recognition 56 includes a pattern recognition unit 56a which in responsive to an image captured by the camera, obtains information relating to the image. The pattern recognition unit 56a includes an edge recognition unit 56b that interpret a shape (e.g., including one or more corners/edges) of a beverage container. A bar code may be read or scanned using a bar code reader responsive to a bar code in the image. The image recognition 56 may include the bar code reader (not shown in FIG. 4). Finally a database 57 is used to store data on each user of the system in a secure manner. The platform 5 may also include a display unit (not shown in FIG. 4) that displays a BAC of the user.

With reference to FIGS. 1 through 4, FIG. 5 illustrates the operation of the image recognition algorithm 33 on the smartphone 3 according an embodiment herein. Once the user captures an image (e.g., a photograph) of the drink using the camera 11 on their phone, the user will click an "identify drink" button on the phone and the application will be initiated. A signal is sent to the platform 5, including an image of either the beverage container or glass, or an image of the bar code on the beverage container. The image recognition software on the platform 5 will interpret the shape of the container or branding, present in the image (e.g., photograph), using edge detection technology and send a number of drink options for display on the phone display for the user to select from. A record of the alcohol consumption can be recorded in a data record 35 on the phone. Alternatively, if the user scans the bar code on the drinks container in order to capture the identity of their drink, this is then interpreted by a bar code reader at the platform 5.

Figure 6:
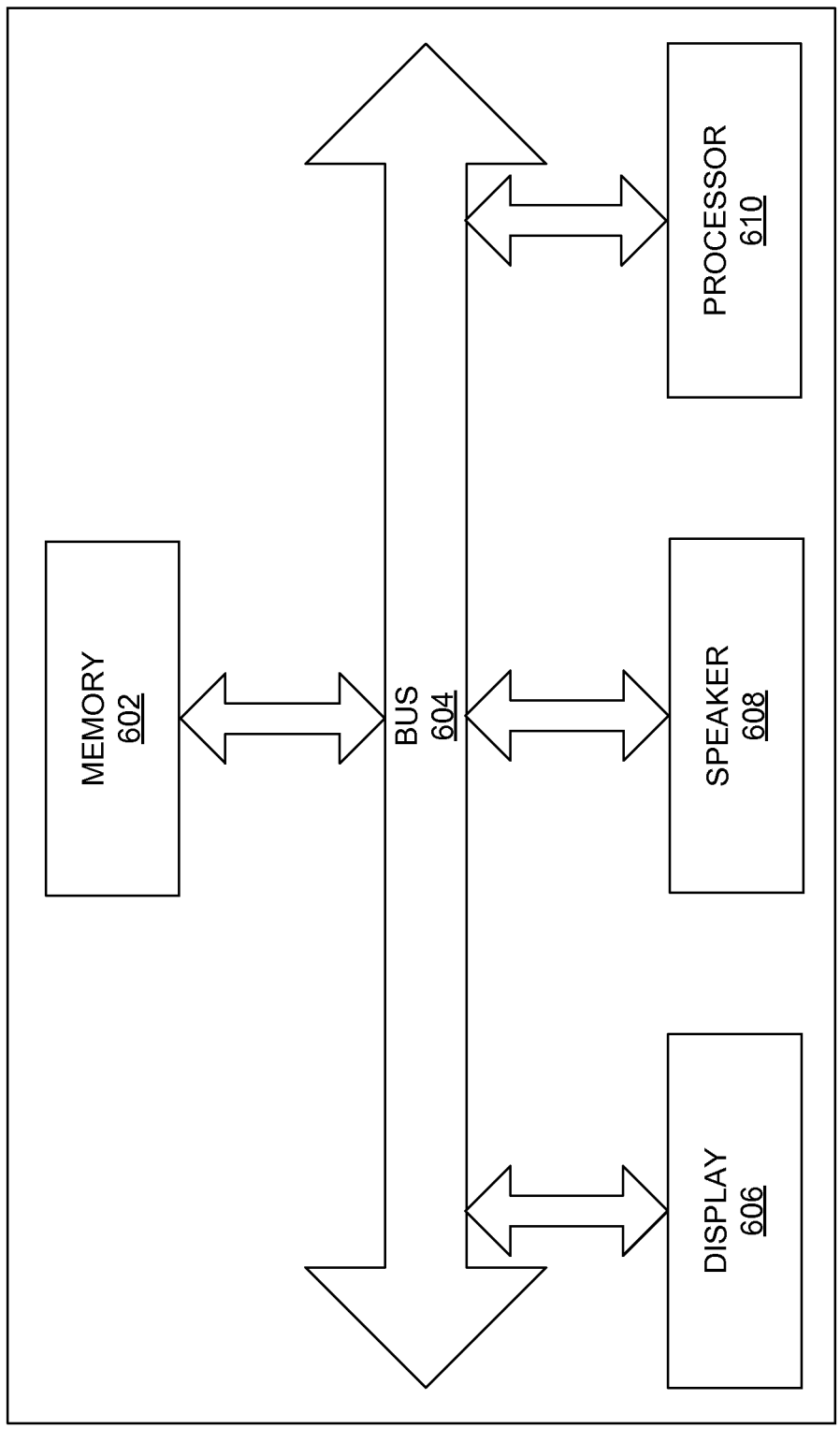
FIG. 6 illustrates an exploded view of the one or more smartphones used in accordance with the embodiments herein.

FIG. 6 illustrates an exploded view of the smartphones 3a, 3b, and 3c having a memory 602 having a set of computer instructions, a bus 604, a display 606, a speaker 608, and a processor 610 capable of processing a set of instructions to perform any one or more of the methodologies herein, according to an embodiment herein. The processor 610 may also enable digital content to be consumed in the form of video for output via one or more displays 606 or audio for output via speaker and/or earphones 608. The processor 610 may also carry out the methods described herein and in accordance with the embodiments herein.

Digital content may also be stored in the memory 602 for future processing or consumption. The memory 602 may also store program specific information and/or service information (PSI/SI), including information about digital content (e.g., the detected information bits) available in the future or stored from the past. A user of the one or more mobile communication devices (i.e. smartphones 3a, 3b, and 3c) may view this stored information on display 606 and select an item of for viewing, listening, or other uses via input, which may take the form of keypad, scroll, or other input device(s) or combinations thereof. When digital content is selected, the processor 610 may pass information. The content and PSI/SI may be passed among functions within the one or more mobile communication devices (i.e. smartphones 3a, 3b, and 3c) using the bus 604.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly.

The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can take the form of, an entirely hardware embodiment, an entirely software embodiment or an embodiment including both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, remote controls, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 7:
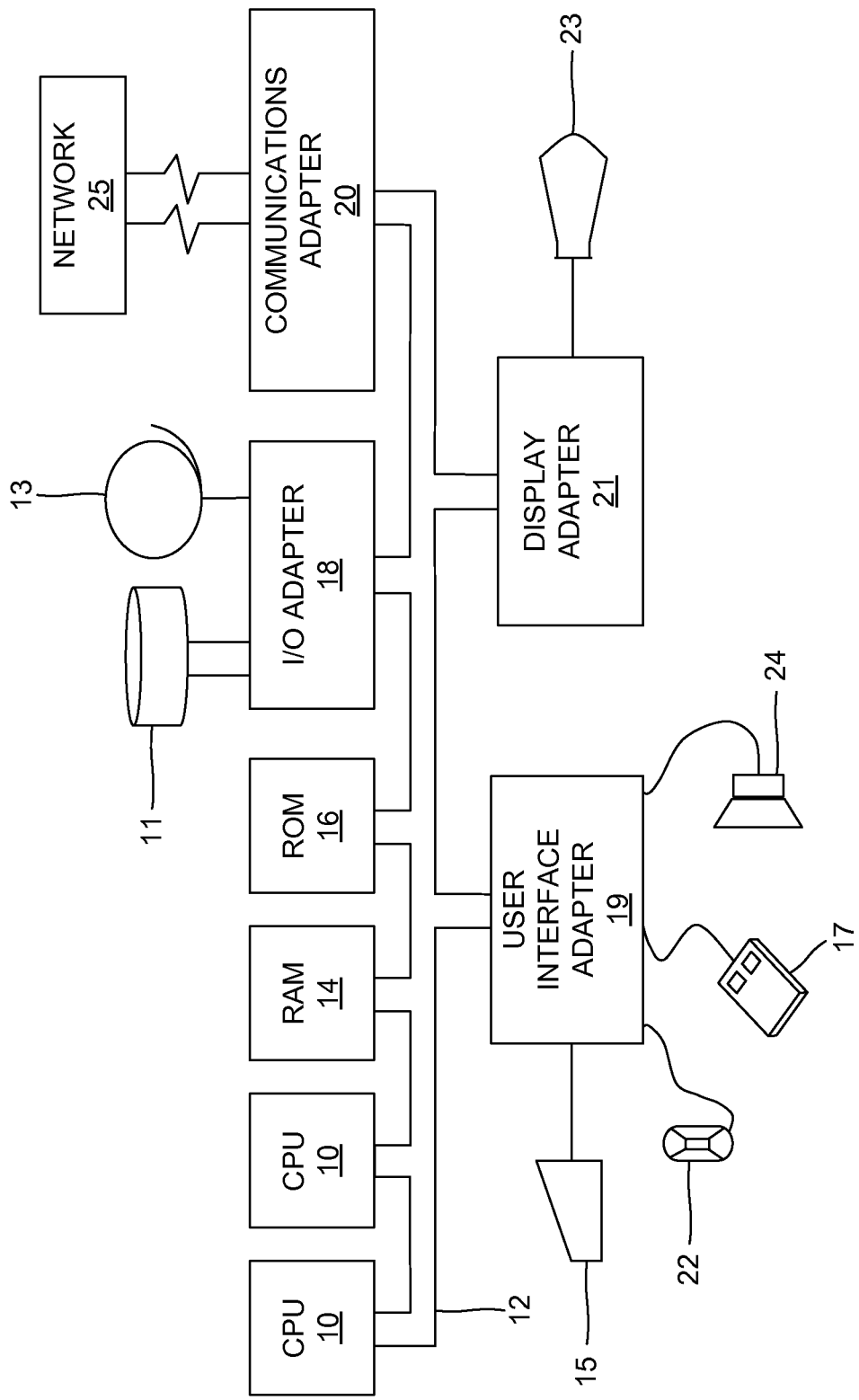
FIG. 7 illustrates a schematic diagram of a computer architecture used in accordance with the embodiments herein.

A representative hardware environment for practicing the embodiments herein is depicted in FIG. 7. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein.

The system further includes a user interface adapter 19 that connects a keyboard 15, mouse 17, speaker 24, microphone 22, and/or other user interface devices such as a touch screen device (not shown) or a remote control to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The alcohol management system includes a breathalyzer of a portable nature, which can be used by an individual to monitor their alcohol consumption. The alcohol management system has particular application in giving the individual the possibility of being able to adjust their drinking behavior if necessary, based on information provided by the breathalyzer.

It will be appreciated that whilst it is advantageous to install the image recognition software on the platform 5 to reduce the amount of software installed on each phone 13, the image recognition software may be installed on the mobile device if it has sufficient memory.

Thus by the use of the overall system including the individual disposable breathalyzer units, the application on the smartphone including the ability to easily obtain a record of the drinks consumed from images produced by the phone camera and the backup to each user provided by the platform 5, it is possible to produce cognitive feedback loops with the individuals and encourage the individuals towards lower alcohol consumption.

It will be appreciated that an alcohol management system and the embodiments described herein may be readily individualized for the user. As the breathalyzer unit is convenient to use and disposable, a user can be encouraged to use such a system.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A blood alcohol content (BAC) measurement system powered by an audio signal received from an audio jack of a phone, said BAC measurement system comprising:
   (a) a plug adapted to be inserted in the audio jack of the phone; and
   (b) a breathalyzer unit, wherein said breathalyzer unit comprises:
      (i) a sensor unit comprising a fuel cell that generates an electric current when a breath of a user contacts the fuel cell;
      (ii) a microcontroller that generates a signal based on the electric current, wherein a frequency of the signal is based on an alcohol content in the breath; and
      (iii) a power extraction unit that is coupled to the plug, wherein said power extraction unit is adapted to
         (a) receive the audio signal from the audio jack of the phone; and
         (b) convert the audio signal into power for powering the sensor unit without storing the power in a battery, wherein the audio signal is generated by the phone, wherein the phone comprises:
            (a) a processor;
            (b) a memory unit;
            (c) a camera that captures an image of an alcoholic drink;
            (d) a pattern recognition unit responsive to an image captured by the camera, that obtains information relating to the image; and
            (e) an alcohol consumption manager, executed by the processor, that updates a BAC of the user based on (i) the frequency of the signal generated by the microcontroller and (ii) the information relating to the image.

2. The blood alcohol content (BAC) measurement system of claim 1, wherein the pattern recognition means comprises edge recognition means to interpret a shape of a beverage container.

3. The blood alcohol content (BAC) measurement system of claim 1, wherein the pattern recognition means comprises a bar code reader responsive to a bar code in the image.

4. The blood alcohol content (BAC) measurement system of claim 1, wherein a frequency of the audio signal ranges from 15000 Hz to 18000 Hz.

5. A blood alcohol content (BAC) measurement system comprising:
   (i) a breathalyzer unit that comprises
      (a) a sensor unit comprising a fuel cell that generates an electric current when a breath of a user contacts the fuel cell;
      (b) a microcontroller that generates a signal based on the electric current, wherein a frequency of the signal is based on an alcohol content in the breath; and
      (c) a power extraction unit that is coupled to one end of a plug to receive an audio signal, wherein said power extraction unit is adapted to convert the audio signal into power for powering the sensor unit without storing the power in a battery; and
   (ii) a phone that generates the audio signal, wherein the audio signal is communicated from an audio jack of the phone to the power extraction unit through the plug that is coupled to the audio jack at its other end, wherein the phone comprises:
      (a) a processor;
      (b) a memory unit;
      (c) a camera that captures an image of an alcoholic drink, (d) a pattern recognition unit responsive to an image captured by the camera, that obtains information relating to the image;

(e) an alcohol consumption manager, executed by the processor, that updates a BAC of the user based on (i) the frequency of the signal generated by the microcontroller and (ii) the information relating to the image; and (f) a display unit that displays the BAC of the user.

6. The blood alcohol content (BAC) measurement system of claim 5, wherein the phone further comprises an input unit that receives input from a user on drink options generated based on the information relating to the image.

7. The blood alcohol content (BAC) measurement system of claim 5, wherein the breathalyzer unit is connected to the phone through an audio jack of the phone.

* * * * *